United States Patent

Iyer

(10) Patent No.: US 8,331,077 B2
(45) Date of Patent: Dec. 11, 2012

(54) CAPACITOR FOR FILTERED FEEDTHROUGH WITH ANNULAR MEMBER

(75) Inventor: Rajesh V. Iyer, Eden Praire, MN (US)

(73) Assignee: Medtronic, Inc., Minneapolis, MN (US)

( * ) Notice: Subject to any disclaimer, the term of this patent is extended or adjusted under 35 U.S.C. 154(b) by 428 days.

(21) Appl. No.: 12/571,051

(22) Filed: Sep. 30, 2009

(65) Prior Publication Data

US 2010/0179606 A1    Jul. 15, 2010

Related U.S. Application Data

(63) Continuation-in-part of application No. 12/351,946, filed on Jan. 12, 2009.

(51) Int. Cl.
*H01G 4/30* (2006.01)
*H01G 4/35* (2006.01)
*H01G 4/228* (2006.01)
*H01G 4/236* (2006.01)

(52) U.S. Cl. .................. 361/302; 361/301.4; 361/306.1; 361/307

(58) Field of Classification Search ............... 361/306.3, 361/301.4, 302
See application file for complete search history.

(56) References Cited

U.S. PATENT DOCUMENTS

| | | |
|---|---|---|
| 3,646,405 A | 2/1972 | Wallis et al. |
| 3,803,875 A | 4/1974 | Root et al. |
| 3,920,888 A | 11/1975 | Barr |
| 4,152,540 A | 5/1979 | Duncan et al. |
| 4,285,730 A | 8/1981 | Sanford et al. |
| 4,314,031 A | 2/1982 | Sanford et al. |
| 4,323,654 A | 4/1982 | Tick et al. |
| 4,420,569 A | 12/1983 | Tick |
| 4,421,947 A | 12/1983 | Kyle |
| 4,424,551 A | 1/1984 | Stevenson et al. |
| 4,940,858 A | 7/1990 | Taylor et al. |
| 4,943,686 A | 7/1990 | Kucharek |
| 5,015,530 A | 5/1991 | Brow et al. |
| 5,021,307 A | 6/1991 | Brow et al. |
| 5,089,446 A | 2/1992 | Cornelius et al. |
| 5,104,738 A | 4/1992 | Brow et al. |
| 5,104,755 A | 4/1992 | Taylor et al. |
| 5,175,067 A | 12/1992 | Taylor et al. |
| 5,242,097 A | 9/1993 | Socha |

(Continued)

FOREIGN PATENT DOCUMENTS

DE    8631853    11/1988

(Continued)

OTHER PUBLICATIONS (PCT/US2010/020748) PCT Notification of Transmittal of the International Search Report and the Written Opinion of the International Searching Authority.

(Continued)

*Primary Examiner* — Eric Thomas
*Assistant Examiner* — Arun Ramaswamy

(57) ABSTRACT

A filtered feedthrough assembly includes a capacitor comprising a top portion, a bottom portion, an outer diameter portion and an inner diameter portion. The inner diameter portion defines at least one aperture extending from the top portion to the bottom portion. A conductive annular member is placed onto the top portion around the at least one aperture. A feedthrough pin extends through each of the apertures and is soldered to the inner diameter portion of the capacitor by application of a solder preform upon the conductive pad of conductive material.

16 Claims, 9 Drawing Sheets

U.S. PATENT DOCUMENTS

| | | | |
|---|---|---|---|
| 5,294,241 A | 3/1994 | Taylor et al. |
| 5,306,581 A | 4/1994 | Taylor et al. |
| 5,333,095 A | 7/1994 | Stevenson et al. |
| 5,648,302 A | 7/1997 | Brow et al. |
| 5,650,759 A | 7/1997 | Hittman et al. |
| 5,693,580 A | 12/1997 | Brow et al. |
| 5,817,984 A | 10/1998 | Taylor et al. |
| 5,821,011 A | 10/1998 | Taylor et al. |
| 5,825,608 A | 10/1998 | Duva et al. |
| 5,851,222 A | 12/1998 | Taylor et al. |
| 5,866,851 A | 2/1999 | Taylor et al. |
| 5,867,361 A | 2/1999 | Wolf et al. |
| 5,870,272 A | 2/1999 | Seifried et al. |
| 5,871,513 A | 2/1999 | Taylor et al. |
| 5,902,326 A | 5/1999 | Lessar et al. |
| 6,031,710 A | 2/2000 | Wolf et al. |
| 6,076,017 A | 6/2000 | Taylor et al. |
| 6,090,503 A | 7/2000 | Taylor et al. |
| 6,275,369 B1 | 8/2001 | Stevenson et al. |
| 6,349,025 B1 | 2/2002 | Fraley et al. |
| 6,536,882 B2 | 3/2003 | Hawkins et al. |
| 6,566,978 B2 | 5/2003 | Stevenson et al. |
| 6,603,182 B1 | 8/2003 | Low et al. |
| 6,643,903 B2 | 11/2003 | Stevenson et al. |
| 6,660,116 B2 | 12/2003 | Wolf et al. |
| 6,759,163 B2 | 7/2004 | Frysz et al. |
| 6,759,309 B2 | 7/2004 | Gross |
| 6,768,629 B1 | 7/2004 | Allen et al. |
| 6,855,456 B2 | 2/2005 | Taylor et al. |
| 6,888,233 B2 | 5/2005 | Horning et al. |
| 6,924,165 B2 | 8/2005 | Horning et al. |
| 7,046,499 B1 | 5/2006 | Imani et al. |
| 7,094,967 B2 | 8/2006 | Evans et al. |
| 7,098,117 B2 | 8/2006 | Najafi et al. |
| 7,210,966 B2 | 5/2007 | Taylor et al. |
| 7,214,441 B2 | 5/2007 | Cortright et al. |
| 7,260,434 B1 | 8/2007 | Lim et al. |
| 7,281,305 B1 | 10/2007 | Iyer et al. |
| 7,285,509 B2 | 10/2007 | Bayya et al. |
| 7,310,216 B2 * | 12/2007 | Stevenson et al. ............ 361/302 |
| 2001/0050837 A1 | 12/2001 | Stevenson et al. |
| 2003/0083715 A1 | 5/2003 | Taylor et al. |
| 2003/0123215 A1 | 7/2003 | Allen et al. |
| 2003/0125185 A1 | 7/2003 | Hirose |
| 2003/0179536 A1 | 9/2003 | Stevenson et al. |
| 2004/0126953 A1 | 7/2004 | Cheung |
| 2004/0152229 A1 | 8/2004 | Najafi et al. |
| 2004/0180464 A1 | 9/2004 | Horning et al. |
| 2004/0244484 A1 | 12/2004 | Horning et al. |
| 2005/0060003 A1 | 3/2005 | Taylor et al. |
| 2005/0092507 A1 | 5/2005 | Marshall et al. |
| 2005/0186823 A1 | 8/2005 | Ring et al. |
| 2006/0009813 A1 | 1/2006 | Taylor et al. |
| 2006/0173506 A1 | 8/2006 | Rusin et al. |
| 2006/0192272 A1 | 8/2006 | Receveur et al. |
| 2006/0247714 A1 | 11/2006 | Taylor et al. |
| 2006/0290257 A1 | 12/2006 | Heo et al. |
| 2007/0004580 A1 | 1/2007 | Kass |
| 2007/0179553 A1 * | 8/2007 | Iyer et al. ........................ 607/37 |
| 2007/0179554 A1 | 8/2007 | Iyer et al. |
| 2007/0179555 A1 | 8/2007 | Iyer et al. |
| 2007/0217121 A1 | 9/2007 | Fu et al. |
| 2007/0234540 A1 | 10/2007 | Iyer et al. |
| 2007/0239223 A1 | 10/2007 | Engmark et al. |
| 2007/0260282 A1 | 11/2007 | Taylor et al. |
| 2008/0060844 A1 | 3/2008 | Teske et al. |
| 2008/0118831 A1 | 5/2008 | Jouanneau-Si-Larbi et al. |
| 2009/0079517 A1 | 3/2009 | Iyer |
| 2009/0079518 A1 | 3/2009 | Iyer |
| 2009/0079519 A1 | 3/2009 | Iyer |

FOREIGN PATENT DOCUMENTS

| | | | |
|---|---|---|---|
| EP | 0404435 A1 | 12/1990 |
| EP | 0404435 B1 | 9/1996 |
| EP | 1 760 735 A1 | 3/2007 |
| WO | WO 03/073450 A1 | 9/2003 |
| WO | WO 2009/039006 A1 | 3/2009 |

OTHER PUBLICATIONS

DIEMAT DM2995PF Series Lead (PB)-Free Sealing Glass Preforms—Preliminary Data Sheet, Aug. 27, 2006, 4 pages.

DIEMAT DM2700PF Series, DM2700PF/DM2760PF, Low-Temperature Sealing Glass Preforms—Product Data Sheet, Jul. 24, 2006, 4 pages.

DIEMAT, Inc. Material Safety Data Sheet—DM2995PF, Aug. 23, 2006, 4 pages.

International Search Report for PCT/US2009/050191 dated Oct. 6, 2009, 4 pages.

International Search Report for PCT/US2008/077179 dated May 25, 2009, 4 pages.

Yourassowsky, E. et al., Combination of minocycline and rifampicin against methicillin- and gentamicin-resistant *Staphylococcus aureus*, J Clin Pathol 1981; 34:559-563.

Bayston, R. et al., Antimicrobial activity of silicone rubber used in hydrocephalus shunts, after impregnation with antimicrobial substances, J Clin Pathol 1981; 34:1057-1062.

* cited by examiner

CAPACITOR FOR FILTERED FEEDTHROUGH WITH ANNULAR MEMBER

RELATED APPLICATION

This application is a continuation-in-part of U.S. patent application Ser. No. 12/351,946, filed Jan. 12, 2009 entitled "Capacitor for Filtered Feedthrough with Conductive Pad", herein incorporated by reference in its entirety.

FIELD

The present disclosure relates to electrical feedthroughs for implantable medical devices and, more particularly, an improved capacitor assembly for a filtered feedthrough.

BACKGROUND

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

Electrical feedthroughs serve the purpose of providing an electrical circuit path extending from the interior of a hermetically sealed container to an external point outside the container. A conductive path is provided through the feedthrough by a conductor pin which is electrically insulated from the container. Many feedthroughs are known in the art that provide the electrical path and seal the electrical container from its ambient environment. Such feedthroughs typically include a ferrule, the conductor pin or lead and a hermetic glass or ceramic seal which supports the pin within the ferrule. Such feedthroughs are typically used in electrical medical devices such as implantable pulse generators (IPGs). It is known that such electrical devices can, under some circumstances, be susceptible to electromagnetic interference (EMI). At certain frequencies for example, EMI can inhibit pacing in an IPG. This problem has been addressed by incorporating a capacitor structure within the feedthrough ferrule, thus shunting any EMI at the entrance to the IPG for high frequencies. This has been accomplished with the aforementioned capacitor device by combining it with the feedthrough and incorporating it directly into the feedthrough ferrule. Typically, the capacitor electrically contacts the pin lead and the ferrule.

Many different insulator structures and related mounting methods are known in the art for use in medical devices wherein the insulator structure also provides a hermetic seal to prevent entry of body fluids into the housing of the medical device. The feedthrough terminal pins, however, are connected to one or more lead wires which effectively act as an antenna and thus tend to collect stray or electromagnetic interference (EMI) signals for transmission to the interior of the medical device. In some prior art devices, ceramic chip capacitors are added to the internal electronics to filter and thus control the effects of such interference signals. This internal, so-called "on-board" filtering technique has potentially serious disadvantages due to intrinsic parasitic resonances of the chip capacitors and EMI radiation entering the interior of the device housing.

In another and normally preferred approach, a filter capacitor is combined directly with a terminal pin assembly to decouple interference signals to the housing of the medical device. In a typical construction, a coaxial feedthrough filter capacitor is connected to a feedthrough assembly to suppress and decouple undesired interference or noise transmission along a terminal pin.

So-called discoidal capacitors having two sets of electrode plates embedded in spaced relation within an insulative substrate or base typically form a ceramic monolith in such capacitors. One set of the electrode plates is electrically connected at an inner diameter surface of the discoidal structure to the conductive terminal pin utilized to pass the desired electrical signal or signals. The other or second set of electrode plates is coupled at an outer diameter surface of the discoidal capacitor to a cylindrical ferrule of conductive material, wherein the ferrule is electrically connected in turn to the conductive housing or case of the electronic instrument.

In operation, the discoidal capacitor permits passage of relatively low frequency electrical signals along the terminal pin, while shunting and shielding undesired interference signals of typically high frequency to the conductive housing. Feedthrough capacitors of this general type are commonly employed in implantable pacemakers, defibrillators and the like, wherein a device housing is constructed from a conductive biocompatible metal such as titanium and is electrically coupled to the feedthrough filter capacitor. The filter capacitor and terminal pin assembly prevent interference signals from entering the interior of the device housing, where such interference signals might otherwise adversely affect a desired function such as pacing or defibrillating.

In the past, feedthrough filter capacitors for heart pacemakers and the like have typically been constructed by preassembly of the discoidal capacitor with a terminal pin subassembly which includes the conductive terminal pin and ferrule. More specifically, the terminal pin subassembly is prefabricated to include one or more conductive terminal pins supported within the conductive ferrule by means of a hermetically sealed insulator ring or bead. See, for example, the terminal pin subassemblies disclosed in U.S. Pat. Nos. 3,920,888, 4,152,540; 4,421,947; and 4,424,551. The terminal pin subassembly thus defines a small annular space or gap disposed radially between the inner terminal pin and the outer ferrule. A small discoidal capacitor of appropriate size and shape is then installed into this annular space or gap, in conductive relation with the terminal pin and ferrule, e.g., by means of soldering or conductive adhesive. The thus-constructed feedthrough capacitor assembly is then mounted within an opening in the pacemaker housing, with the conductive ferrule in electrical and hermetically sealed relation in respect of the housing, shield or container of the medical device.

Although feedthrough filter capacitor assemblies of the type described above have performed in a generally satisfactory manner, the manufacture and installation of such filter capacitor assemblies has been relatively costly and difficult. For example, installation of the discoidal capacitor into the small annular space between the terminal pin and ferrule can be a difficult and complex multi-step procedure to ensure formation of reliable, high quality electrical connections. Moreover, installation of the capacitor at this location inherently limits the capacitor to a small size and thus also limits the capacitance thereof. Similarly, subsequent attachment of the conductive ferrule to the pacemaker housing, typically by welding or brazing processes or the like, can expose the fragile ceramic discoidal capacitor to temperature variations sufficient to create the risk of capacitor cracking and failure. As described above, a solder, e.g., in the form of a solder preform, may be used to connect the terminal pins with the capacitor. Unfortunately, solder preforms are susceptible to oxidation that may affect the conductivity of the solder and the ability to make a good electrical connection between the pin and the capacitor. Current manufacturing techniques utilize a chemical etching process to remove the formed oxide layers, adding an additional step and expense to the manufacturing process.

There exists, therefore, a significant need for improvements in feedthrough filter capacitor assemblies of the type used, for example, in implantable medical devices such as heart pacemakers and the like, wherein the filter capacitor is designed for relatively simplified and economical, yet highly reliable, installation. In addition, there exists a need for an improved feedthrough assembly that provides reliable and economical electrical connections between the capacitor and feedthrough pins without performing a chemical etching or other process to remove oxide layers from the solder preforms. The present disclosure fulfills these needs and provides further advantages.

SUMMARY

In various embodiments of the present disclosure, a filtered feedthrough assembly is disclosed. The assembly includes a capacitor that has a top portion, a bottom portion, an outer diameter portion and an inner diameter portion. The inner diameter portion defines at least one aperture extending from the top portion to the bottom portion. The capacitor further includes a conductive annular member around the at least one aperture. At least one feedthrough pin extends through the at least one aperture and is soldered to the inner diameter portion of the capacitor by application of a solder preform upon the conductive pad of conductive material. Further areas of applicability of the present disclosure will become apparent from the detailed description, the claims and the drawings. The detailed description and specific examples are intended for purposes of illustration only and are not intended to limit the scope of the disclosure.

BRIEF DESCRIPTION OF DRAWINGS

The present disclosure will become more fully understood from the detailed description and the accompanying drawings, wherein.

DESCRIPTION

Figure 1:
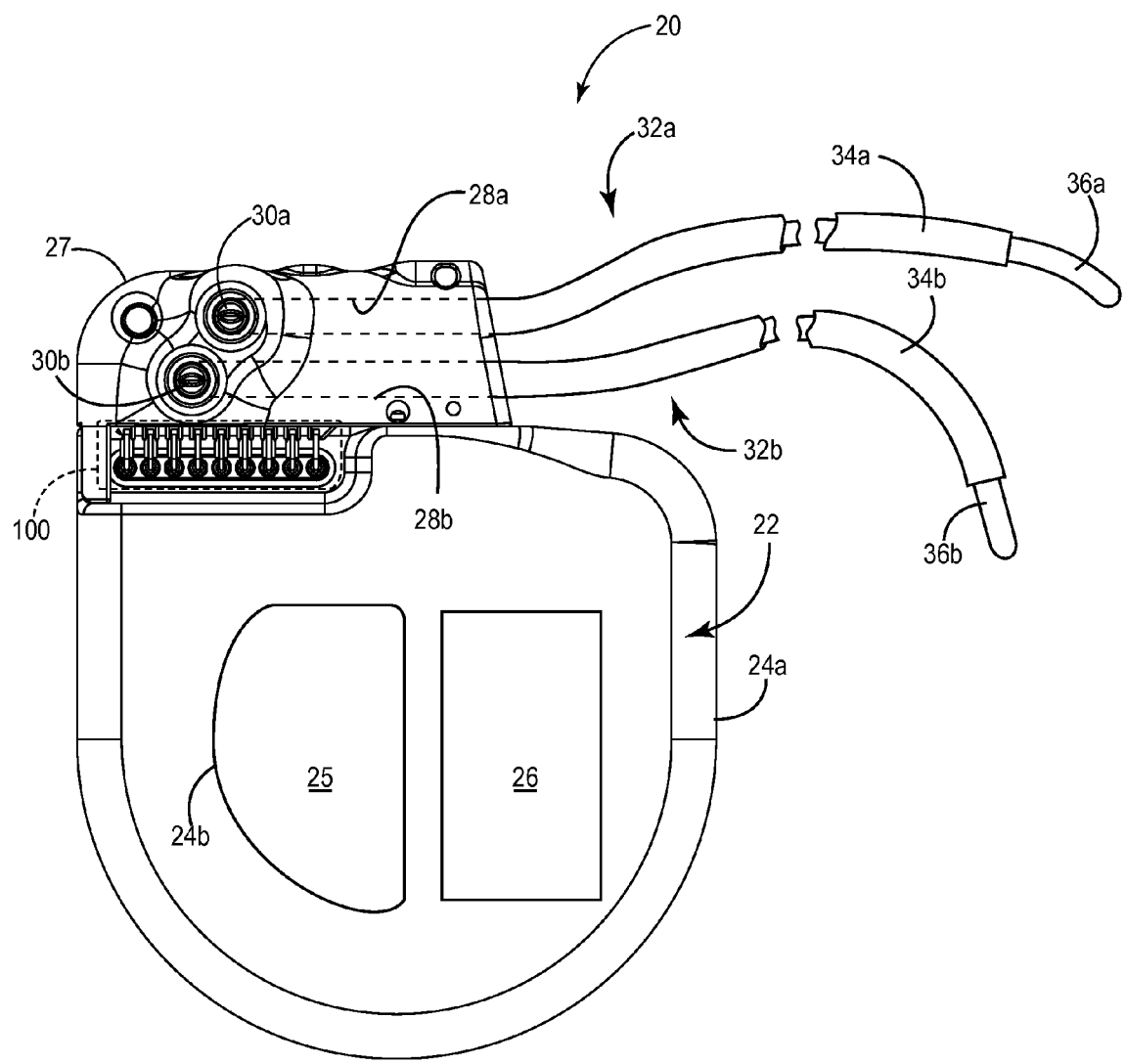
FIG. 1 is a conceptual schematic angled view of an implantable medical device (IMD) in which medical electrical leads extend therefrom.
Figure 2:
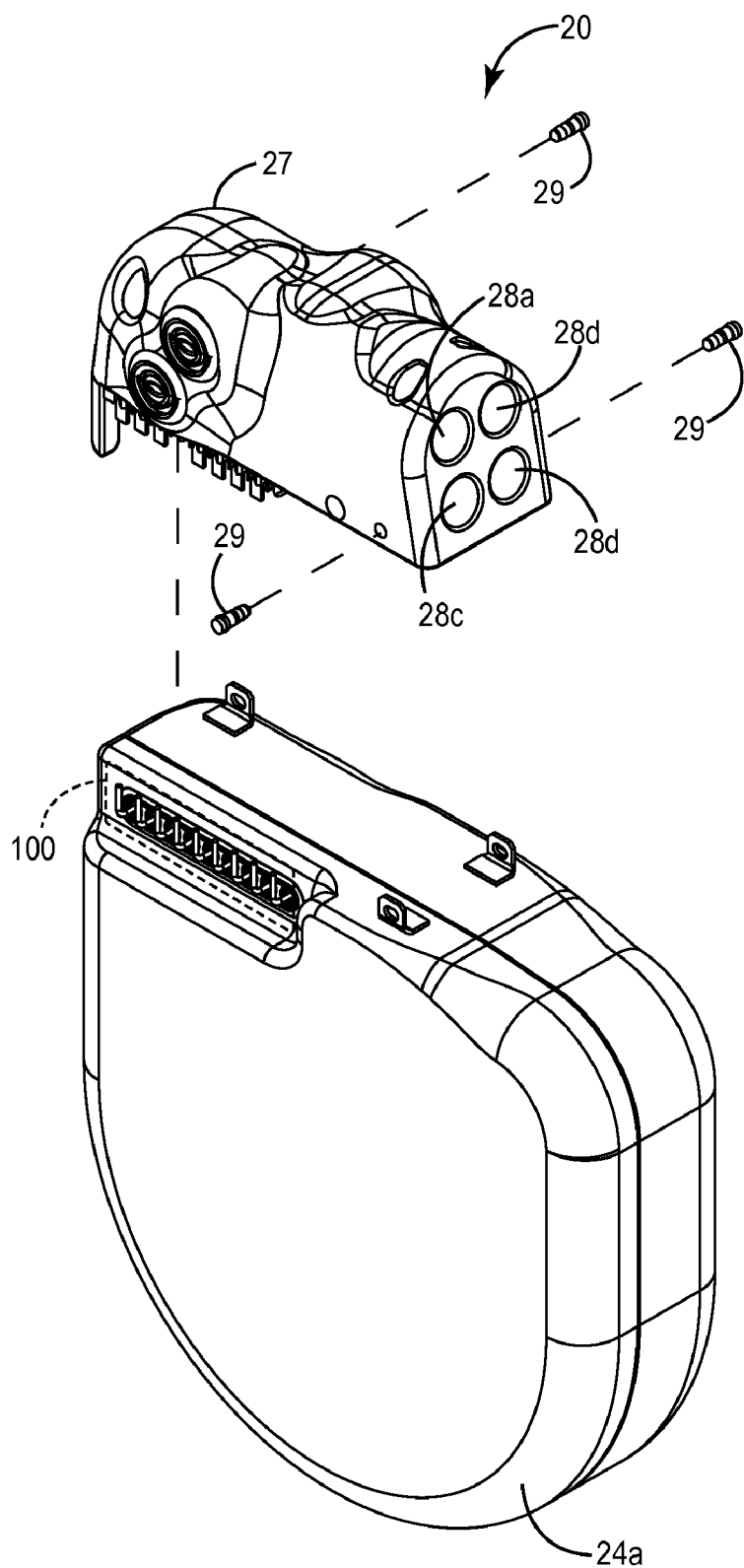
FIG. 2 is a schematic top view of the IMD depicted in FIG. 1.
Figure 3A:
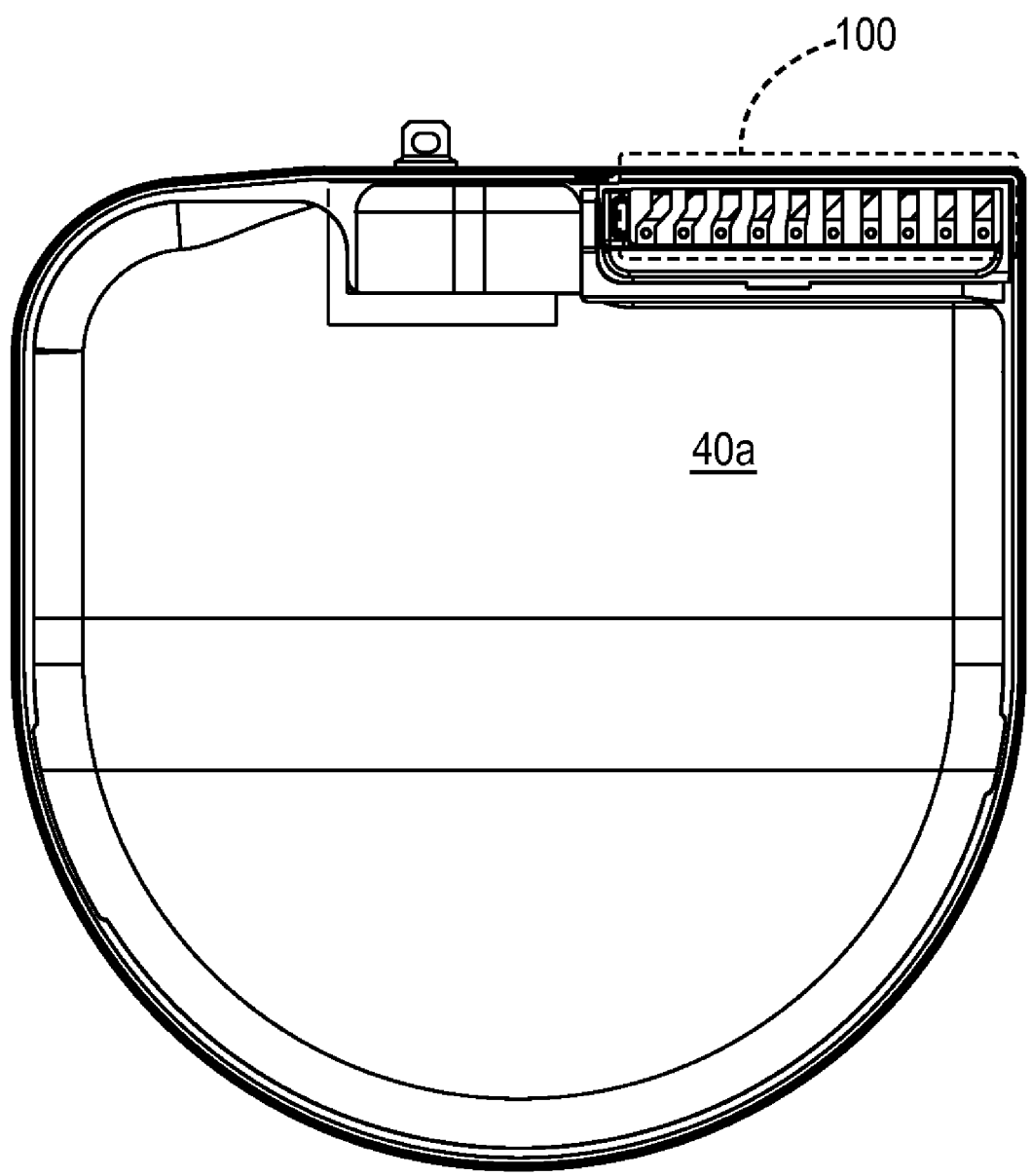
FIG. 3A is a schematic interior view of one side of a housing to an IMD that includes a top side view of a filtered feedthrough electronic module assembly (FFEMA)
Figure 3B:
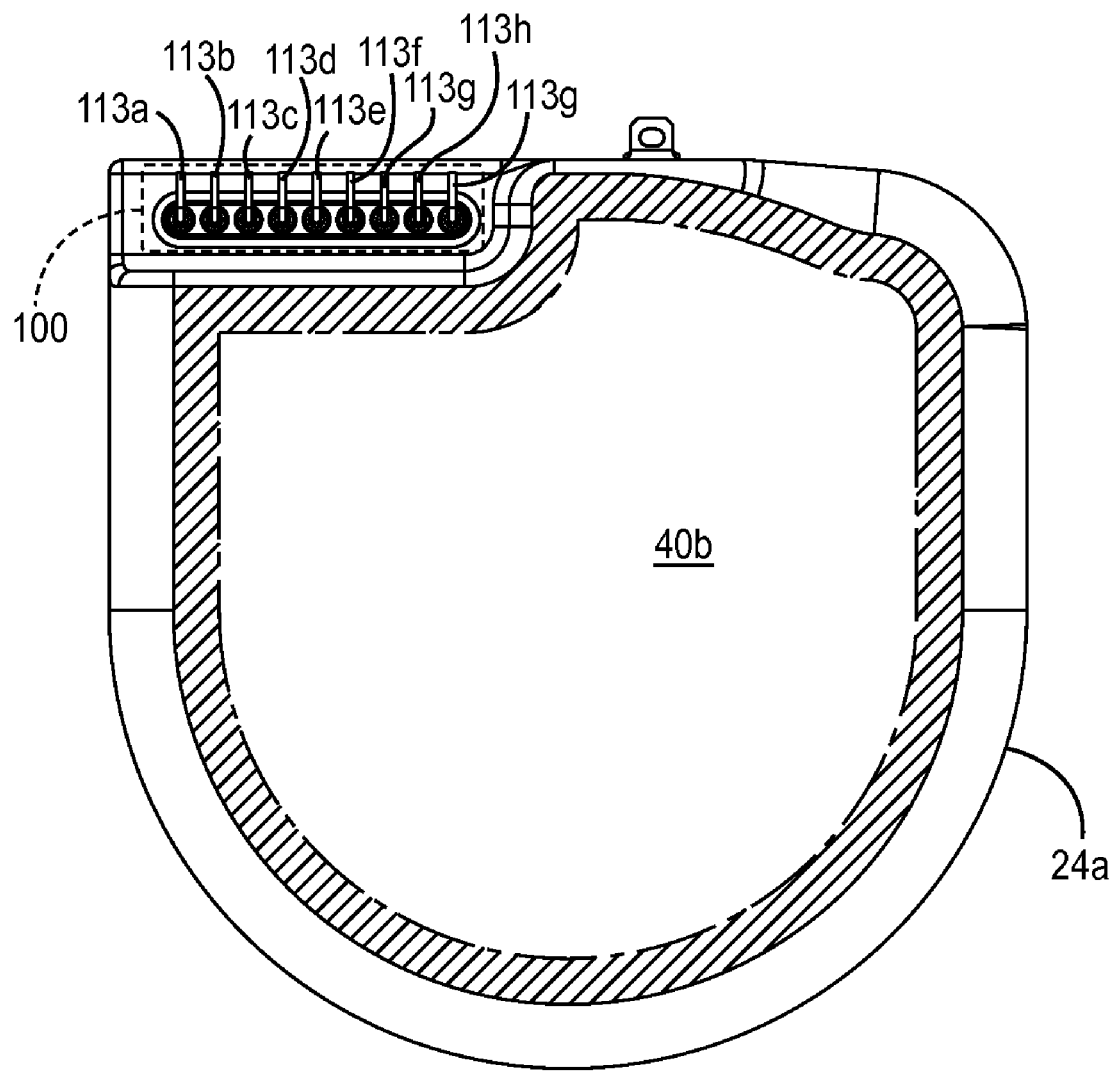
FIG. 3B is a schematic exterior view of the other side of a housing depicted in FIG. 3A to an IMD along with a back side view of a FFEMA.

The following description is merely exemplary in nature and is in no way intended to limit the disclosure, its application, or uses. For purposes of clarity, the same reference numbers will be used in the drawings to identify similar elements. As used herein, the phrase at least one of A, B, and C should be construed to mean a logical (A or B or C), using a non-exclusive logical or. It should be understood that steps within a method may be executed in different order without altering the principles of the present disclosure.

With reference to FIG. 1, an implantable medical device (IMD) 20 can include implantable pacemakers, implantable cardioverter defibrillator (ICD) devices, cardiac resynchronization therapy defibrillator devices, neurostimulators, drug pumps or combinations thereof. Exemplary IMDs are commercially available as including one generally known to those skilled in the art, such as the Medtronic CONCERTO™, SENSIA™, VIRTUOSO™, RESTORE™, RESTORE ULTRA™, sold by Medtronic, Inc. of Minnesota. IMD 20 can include an implantable case, housing or body assembly 22. Implantable case 22 can be formed of appropriate materials and include appropriate features, such as a hermetically sealed body wall 24a. Body wall 24a comprises substantially conductive material such as titanium.

Contained within or associated with case 22 can be a power device 25 such as one or more batteries and/or capacitors encased in housing or case body wall 24b, a controller assembly 26, and a connector body 27. Controller assembly 26 can include a circuit board having a processor, memory, transmitter, receiver, and/or other appropriate portions. Connector body 27 can extend from or be integrated with case 22. At its distal end, connector body 27 can include one or more ports 28a,b that interconnects with one or more connector terminals 30a,b of one or more lead assemblies 32a,b. Exemplary connector bodies 27 can include IS-1 connectors, IS-4 connectors or other suitable connectors. Lead assemblies 32a,b generally include respective lead bodies 34a,b each having a respective tip electrode 36a,b. For example, the first lead assembly 32a can include an active tip electrode 36a and the second lead assembly can include a passive tip electrode 36b.

At its distal end, connector body 27 is connected via connectors or set screws 29 to lead assemblies 32a,b. Set screws 29 force lead assemblies 32a,b in place to form an electrical connection via connector body 27, which, at its proximal end, is connected to a filtered feedthrough electronic module assembly (FFEMA) 100, as depicted in FIGS. 1-3B. FFEMA 100 electrically connects circuitry inside a sealed case of the IMD to a connector body 27, which connects with external components that extend outside of the housing. FFEMA 100 comprises an electronic module assembly (EMA) 102 connected to a feedthrough assembly 120. The EMA 102 is composed of a non-conductive block, referred to as an electronic module block (EMB) 104, with a set of conductive strips 106 or conductive elements connected to the EMB.

Figure 4:
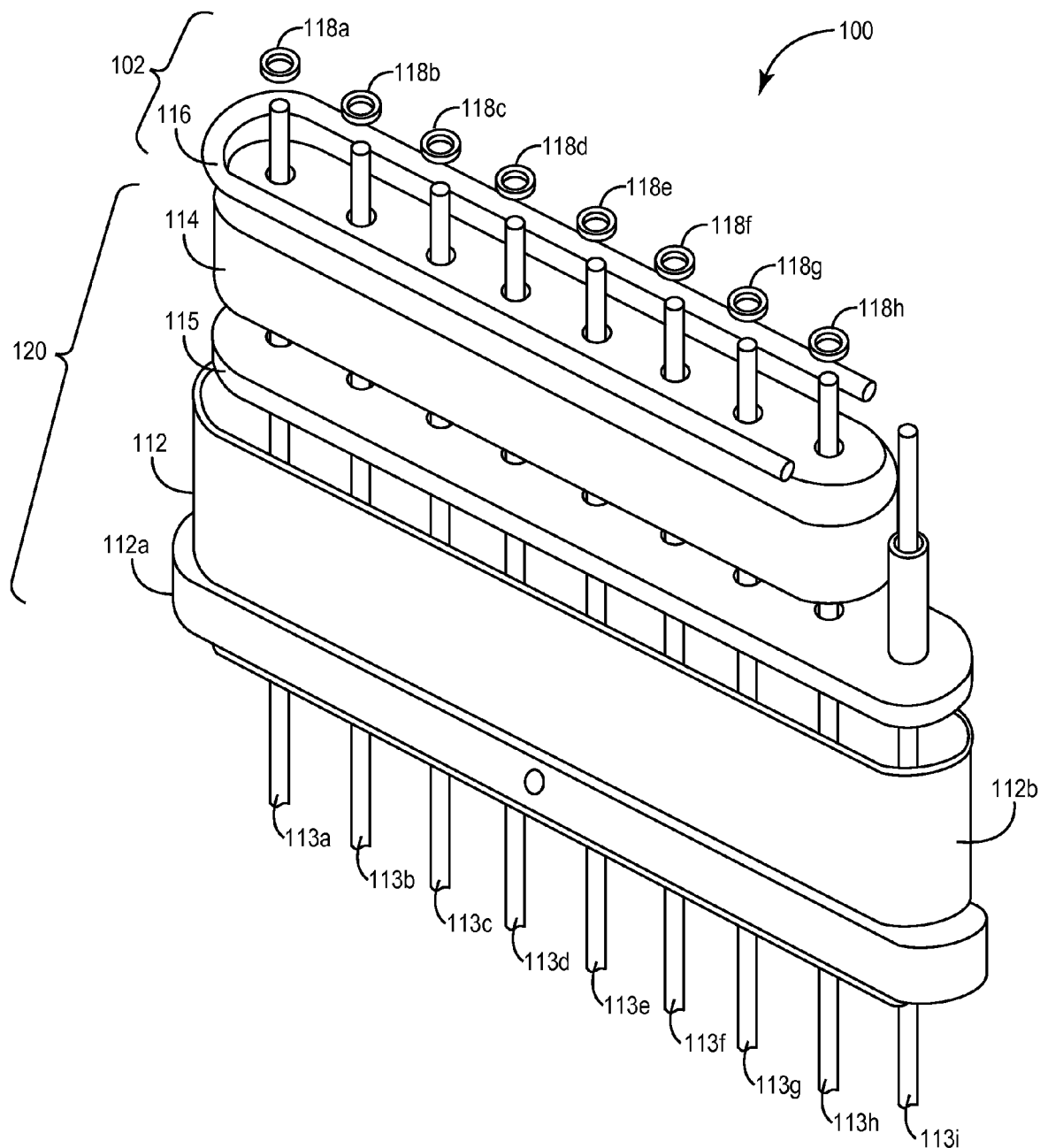
FIG. 4 is an exploded view of a capacitor feedthrough assembly according to various embodiments of the present disclosure.

Referring now to FIG. 4, an exploded view of a capacitor feedthrough assembly 100 according to various embodiments of the present disclosure is illustrated. The assembly 100 comprises a ferrule 112, a plurality of conductor pins 113a-113i, a capacitor 114, a spacer portion 115, a solder bead 116 and a plurality of solder preforms 118a-118h.

The assembly 100 may be manufactured in the following manner. Feedthrough pins 113a-113i are inserted through ferrule 112. In one direction, feedthrough pins 113a-113i extend outside the implanted medical device (not shown), which is hermetically sealed with the bottom portion 112a of the ferrule 112. In the opposite direction, conductor pins 113a-113i extend through a spacer portion 115 and capacitor 114 and into the internal portion of the medical device. The spacer portion 115 provides support for the capacitor 114, and may also inhibit or reduce the flow of solder into the hermetically sealed part of the feedthrough. Once the spacer portion 115 and capacitor 114 are positioned within the top portion 112b of the ferrule 112, electrical connections between the capacitor 114 and conductor pins 113a-113h may be formed.

Figure 5:
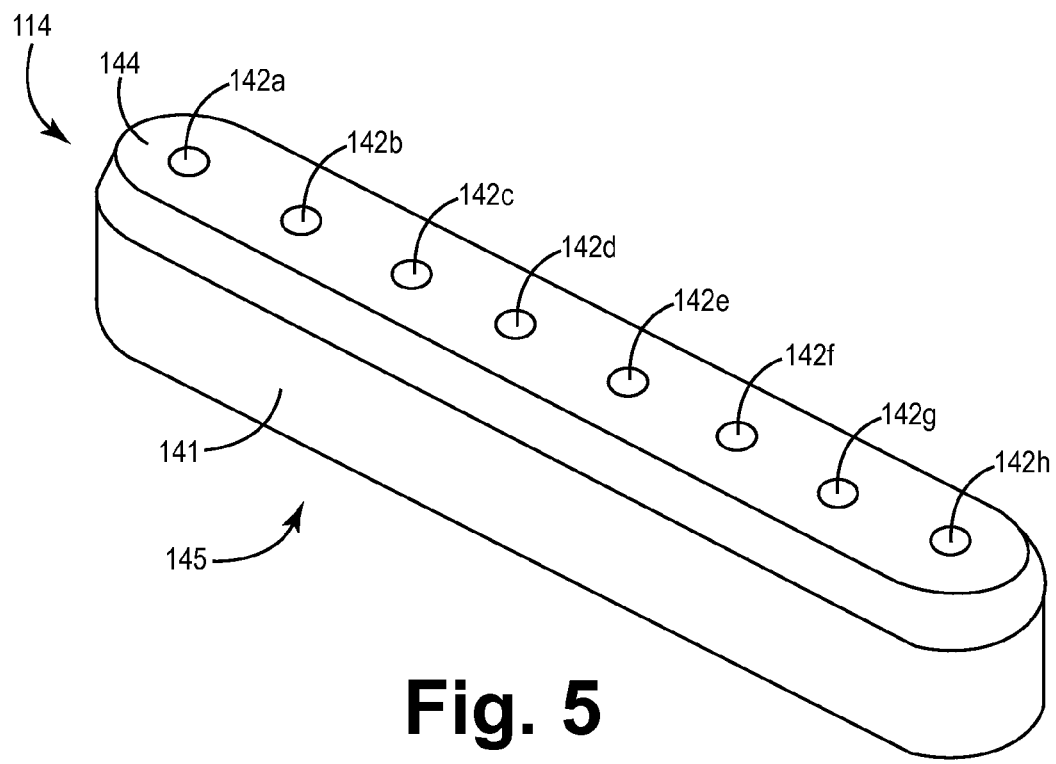
FIG. 5 is a perspective view of a capacitor according to various embodiments of the present disclosure.
Figure 6:
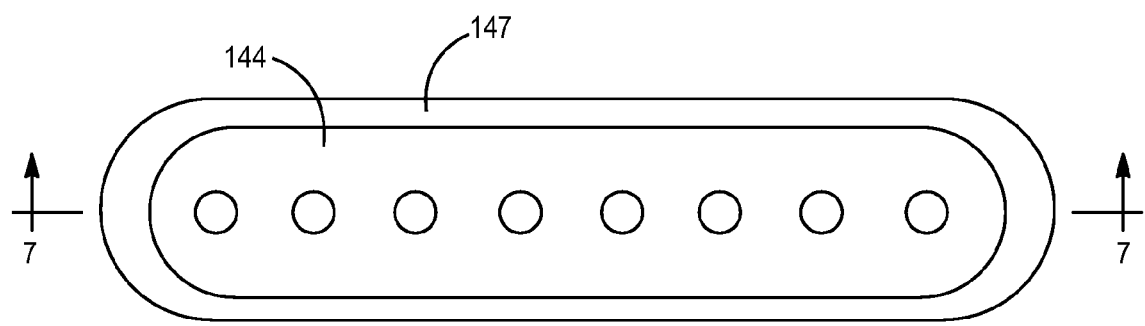
FIG. 6 is a top view of the capacitor of FIG. 5.
Figure 7:
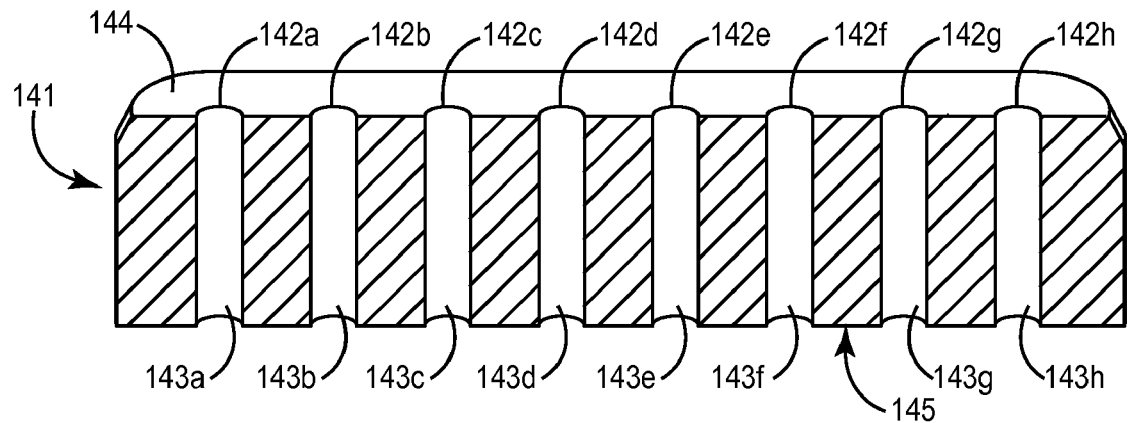
FIG. 7 is a cross-sectional view of the capacitor of FIG. 5 taken along line 7-7.

Referring now to FIGS. 5-7, a capacitor 114 according to various embodiments of the present disclosure is illustrated. The capacitor 114 includes an outer diameter portion 141 that may substantially surround the capacitor 114, a top portion 144 and bottom portion 145. A plurality of feedthrough holes 142a-142h may extend completely through the body of the capacitor 114 to provide an opening between top portion 144 and bottom portion 145. As best illustrated in FIG. 7, inner diameter portion or portions 143a-143h are present in the capacitor 114, and, thus, define the plurality of feedthrough holes 142. The outer diameter portion 141 and inner diameter portion 143 are each connected to one of the two sets of electrode plates that comprise the capacitor 114 and are electrically isolated from one another. In the capacitor feedthrough assembly of FIG. 7, the outer diameter portion 141 is electrically coupled to the ferrule 112 by means of solder bead 116 and the inner diameter portion 143 is coupled to the conductor pins 113a-113h by solder preforms 118a-118h.

A reliable electrical connection between the outer diameter portion 141 and ferrule 112 may be made by the solder bead 116. In one method of assembly according to various embodiments of the present disclosure, the solder bead 16 is placed on top of the capacitor 114 within the top portion 112b of ferrule 112. A chamfer 147 may be formed on the top portion 144 of capacitor 114. The chamfer 147 will bias the placement of solder bead 116 such that proper placement of solder bead 116 is assured. Solder preforms 118a-118h may comprise circular or semi-circular rings of solder material, although the use of other shapes (square, rectangular, triangular, etc.) for the solder preforms 118a-118h are within the scope of this disclosure. Each of the solder preforms 118a-118h receive one of the conductor pins 113a-113h such that the solder preform 118 rests on the top portion 144 of capacitor 114. Once the solder beads 116 and solder preforms 118 are present on the capacitor 114, a solder reflow process is performed, which is described more fully below, in which heat is applied to melt the solder bead 116 and solder preforms 118 in order to electrically connect the ferrule 112 with the outer diameter portion 141 and conductor pins 113 to the inner diameter portion 143. Heat can be applied to assembly 100 by placing assembly 100 into an oven under vacuum. Alternatively, assembly 100 can also be heated with a heat gun or laser.

Figure 8:
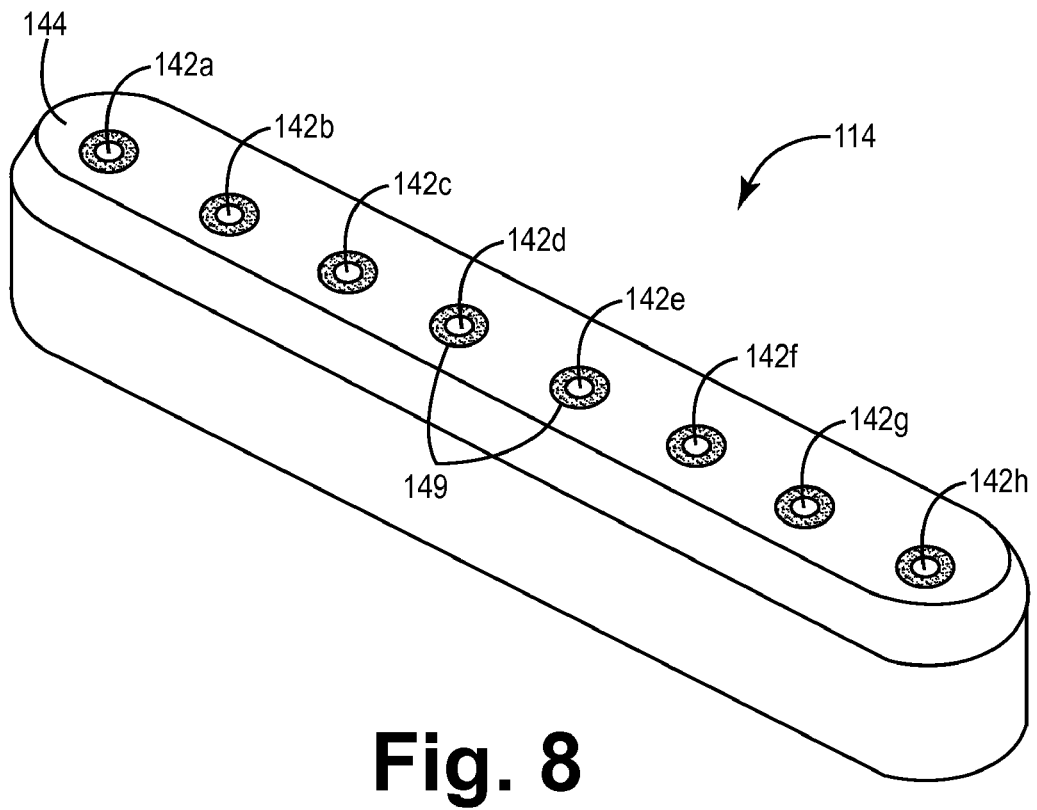
FIG. 8 is a perspective view of a capacitor and associated conductive pads according to various embodiments of the present disclosure.

In various embodiments, solder preforms 118a-118h may comprise fluxless solder. Exemplary fluxless solder can include 90% Indium-10% silver solder alloy. As described above, oxidation may create an oxide layer on the solder preforms, which will inhibit a reliable electrical connection. An oxide layer on the solder preform, and/or oxide formed on the capacitor 114, will inhibit the flow of the solder into the holes 142a-142h and, thus, may lead to inconsistent or imperfect connections between the inner diameter portion 143h and conductor pins 113e-113i of the capacitor feedthrough assembly 100. In order to ensure adequate flow of the solder, a washer may be placed on the top portion 144 of the capacitor 114 surrounding each of the holes 142a-142h, as shown in FIG. 8.

The conductive pad may be applied to the top portion 144 by any means, including, but not limited to, sputtering, manual application, screen printing, ink jet printing, or even application of the capacitor termination material present on the inner diameter portion 143. The presence of the conductive pad 149 provides an enhanced flow of solder from the solder preform 118 into the holes 142 of the inner diameter portion 143 surrounding the conductor pins 113, even if the solder preform has an oxide layer formed on its outside.

Once the capacitor/feedthrough assembly is assembled and the solder bead 116 and solder preforms 118a-118h are present on the capacitor 114, a solder reflow process is performed. The solder reflow process liquefies the solder bead 116 and solder preforms 18 such that solder flows to electrically connect the outer diameter portion 141 and inner diameter portion 143 to the ferrule 112 and conductor pins 113, respectively. The presence of the conductive pads 149 enhance the solder flow such that the connection between the conductor pins 113 and inner diameter portion 143 of capacitor 114 is ensured.

Solder bead 116, in various embodiments of the present disclosure, may be replaced by a different conductive adhesive, e.g., conductive epoxy or brazing. Furthermore, as stated above, the conductive pads may be formed of any conductive material, e.g., gold, silver or silver-palladium. The conductive pads may be formed during the capacitor manufacturing process or may be added to a fully formed capacitor after its manufacture. The solder preforms 118 may be circular of a washer-shaped construction in which the inner diameter is only slightly larger than the diameter of the conductor pins 113 such that proper placement of the solder preforms 118 surrounding the conductor pins 113 is assured. In various embodiments, a counterbore or countersink may be formed around the holes 142 of the capacitor 114 to further assist in the placement of the solder preforms 118, similar to the chamfer 147 present on the outer diameter portion 141 in FIG. 1.

Figure 9:
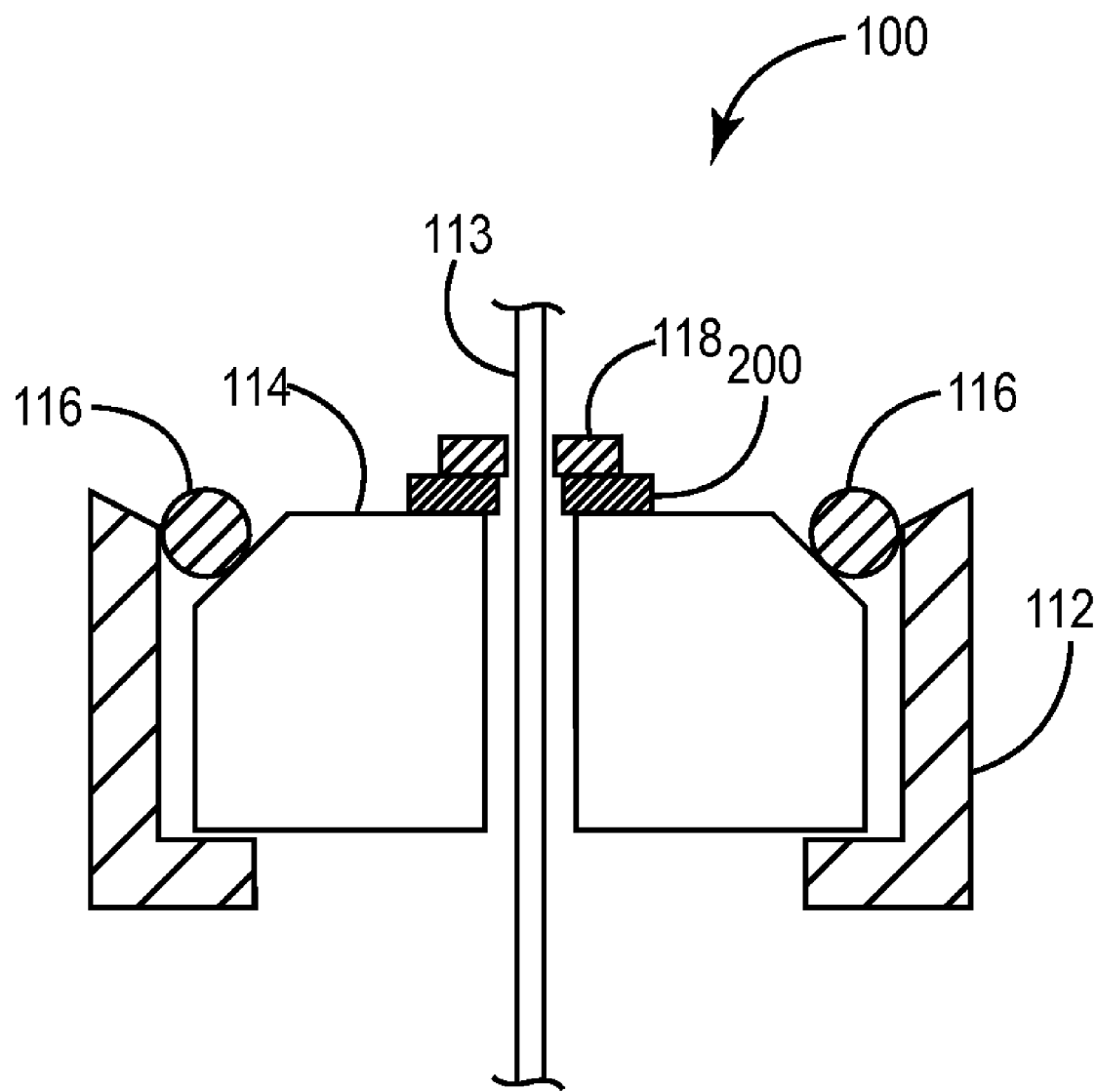
FIG. 9 is a schematic view of a filtered feedthrough assembly.
Figure 10A:
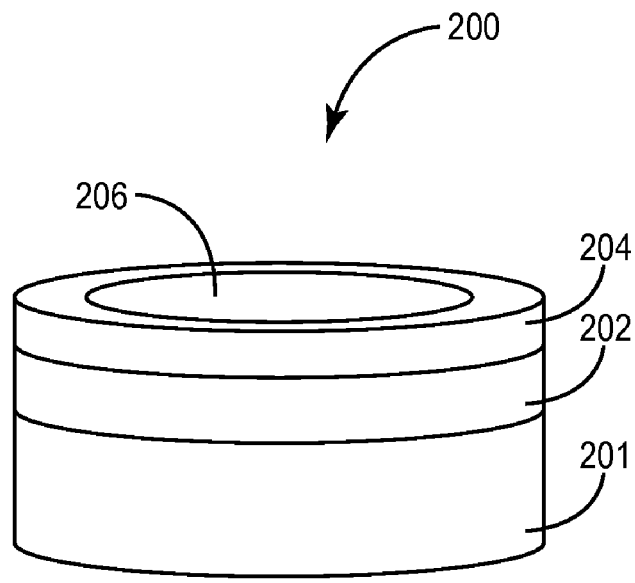
FIG. 10A is a schematic view of an annular member.
Figure 10B:
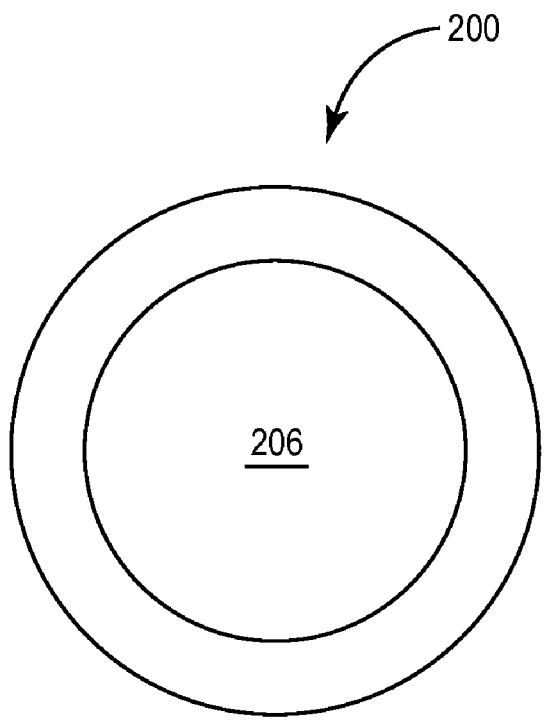
FIG. 10B is a schematic view of a top side of an annular member.

Numerous alternative embodiments exist to bonded pad 149 for ensuring adequate flow of the solder performs 118. For example, a preformed washer or annular member 200, shown in FIGS. 9, and 10A-10B, may be placed on the top portion 144 of the capacitor 114 surrounding each of the holes 142a-142h. In particular, a preformed annular member 200 can be placed over each feedthrough hole 142a-h. Annular member 200 includes an aperture 206 that is only slightly larger than the diameter of the conductor pins 113 such that proper placement of the annular member 200 surrounding the conductor pins 113 is assured. Annular member 200 comprises substrate 201, barrier material 202, anti-oxidation material 204. Substrate 201 can be formed of a metallic material, ceramic material or other suitable material. Exemplary metallic materials used to form substrate 201 includes aluminum, copper, or stainless steel whereas ceramic material can include alumina. Barrier material 202 directly contacts a surface of washer 200. Barrier material 202 reacts with solder and prevents solder from reacting beyond barrier material 202. Barrier material 202 typically comprises nickel to slow a reaction rate of solder during the reflow process. Nickel also ensures that the solder does not react with silver in a silver palladium termination point (not shown) on the capacitor and cause the silver to leach out, which, in turn, could cause the termination point to delaminate from the capacitor 114 itself. Termination point is the area where silver palladium covers the inner diameter portion 143 shown FIG. 7.

Plating or sputter coating can be used to introduce or place barrier material 202 over washer 200. The barrier material 202 comprises nickel; however, other suitable material can be used as well. It will be appreciated that if a plating process is used and nickel is used as a base material, another layer of nickel barrier layer is not required to form barrier material 202. Instead, the base material of nickel serves as the barrier material 202. In this scenario, gold is plated over the nickel substrate 201 to form annular member 200.

An anti-oxidation material 204 is then placed over or onto barrier material 202. Anti-oxidation material 204 can comprise gold, silver, silver-palladium, platinum, platinum-iridium, gold-beryllium, copper, copper-beryllium, nickel, titanium or any combination thereof.

By using annular member 200 instead of sputter coating conductive pad 149 onto top portion 144, a mask design, typically used in sputter coating, is eliminated. Additionally, washer 202 eliminates engineering time used to design a new mask for each new design of a capacitor. The same annular member 202 or ring can be used in multiple capacitor designs. Furthermore, over-sputtering of layers of gold or nickel is eliminated.

It will be appreciated that in one or more embodiments, an annular member 202 can be used with any capacitor for a filtered feedthrough assembly that is formed for an implantable medical device. regardless of whether solder preforms are used. The broad teachings of the disclosure can be implemented in a variety of forms. Therefore, while this disclosure includes particular examples, the true scope of the disclosure should not be so limited since other modifications will become apparent upon a study of the drawings, the specification, and the following claims.

What is claimed is:

1. An implantable medical device comprising:
    a housing;
    a connector body coupled to the housing;
        a filtered feedthrough electronic module assembly (FFEMA) coupled to the connector body, the FFEMA comprising an electronic module assembly (EMA) and a feedthrough assembly coupled to the EMA, a filtered feedthrough assembly, comprising:
        a capacitor comprising a top portion, a bottom portion, an outer diameter portion and an inner diameter portion, wherein said inner diameter portion defines at least one aperture extending from the top portion to the bottom portion and an annular member of conductive material comprising a substrate, a barrier material coated on the substrate and an anti-oxidation material coated on the barrier material is over and contacts the top portion around the at least one aperture; and
        at least one feedthrough pin extending through the at least one aperture, wherein the at least one feedthrough pin is soldered to the inner diameter portion of the capacitor by application of a solder preform upon the annular member of conductive material.

2. The implantable medical device of claim 1, wherein the anti-oxidation material comprises one of gold, silver, silver-palladium, platinum, platinum-iridium, gold-beryllium, copper, copper-beryllium, nickel, titanium and a combination thereof.

3. The implantable medical device of claim 1, wherein a ferrule is coupled to the outer diameter portion of the capacitor by placement of a conductive bead proximate the outer diameter portion and ferrule.

4. The implantable medical device of claim 3, wherein the capacitor further comprises an outer diameter chamfer extending between the outer diameter portion and the top portion and the conductive bead is placed proximate the outer diameter chamfer.

5. The implantable medical device of claim 1, wherein the capacitor further comprises an inner diameter counterbore extending between the inner diameter portion and the top portion and the solder preform is placed proximate the inner diameter counterbore.

6. The implantable medical device of claim 1, wherein the solder preform surrounds the at least one feedthrough pin.

7. A method of manufacturing a filtered feedthrough assembly, comprising:
    placing an annular member onto a capacitor, the annular member includes a substrate, a barrier material coated on the substrate and an anti-oxidation material coated on the barrier material, the capacitor comprising a top portion, a bottom portion, an outer diameter portion and an inner diameter portion, wherein said inner diameter portion defines at least one aperture extending from the top portion to the bottom portion and the annular member is applied to and contacts the top portion around the at least one aperture;
    extending a feedthrough pin through the at least one aperture;
    placing a solder preform upon the annular member; and
    soldering the feedthrough pin to the inner diameter portion of the capacitor with the solder preform.

8. The method of claim 7, wherein the anti-oxidation material comprises one of gold, silver, silver-palladium, platinum, platinum-iridium, gold-beryllium, copper, copper-beryllium, nickel, titanium and a combination thereof.

9. The method of claim 7, further comprising coupling a ferrule to the outer diameter portion of the capacitor.

10. The method of claim 9, further comprising placing a conductive bead proximate the outer diameter portion, wherein the ferrule is coupled to the outer diameter portion of the capacitor by the conductive bead.

11. The method of claim 10, wherein the capacitor further comprises an outer diameter chamfer extending between the outer diameter portion and the top portion and the conductive bead is placed proximate the outer diameter chamfer.

12. The method of claim 11, further comprising placing a spacer within the ferrule, wherein the spacer supports the capacitor.

13. The method of claim 10, wherein the capacitor further comprises an inner diameter counterbore extending between the inner diameter portion and the top portion and the solder preform is placed proximate the inner diameter counterbore.

14. The method of claim 10, wherein the solder preform surrounds the at least one feedthrough pin.

15. A filtered feedthrough assembly, comprising:
    a capacitor comprising a top portion, a bottom portion, an outer diameter portion and an inner diameter portion, wherein said inner diameter portion defines at least one aperture extending from the top portion to the bottom portion and an annular member of conductive material comprising a substrate, a barrier material coated on the substrate and an anti-oxidation material coated on the barrier material is over and contacts the top portion around the at least one aperture; and
    at least one feedthrough pin extending through the at least one aperture, wherein the at least one feedthrough pin is soldered to the inner diameter portion of the capacitor by application of a solder preform upon the annular member of conductive material.

16. The filtered feedthrough of claim 15, wherein the anti-oxidation material comprises one of gold, silver, silver-palladium, platinum, platinum-iridium, gold-beryllium, copper, copper-beryllium, nickel, titanium and a combination thereof.

* * * * *